(12) United States Patent
Shohet et al.

(10) Patent No.: US 11,592,394 B2
(45) Date of Patent: Feb. 28, 2023

(54) METHODS AND SYSTEMS FOR TRANSMISSION AND DETECTION OF FREE RADICALS

(71) Applicant: Wisconsin Alumni Research Foundation, Madison, WI (US)

(72) Inventors: J. Leon Shohet, Madison, WI (US); Michael R. Sussman, Cross Plains, WI (US); Faraz A. Choudhury, Madison, WI (US); Benjamin B. Minkoff, Madison, WI (US); Grzegorz Sabat, Middleton, WI (US); Joshua M. Blatz, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1378 days.

(21) Appl. No.: 15/676,274

(22) Filed: Aug. 14, 2017

(65) Prior Publication Data

US 2018/0045645 A1      Feb. 15, 2018

Related U.S. Application Data

(60) Provisional application No. 62/374,556, filed on Aug. 12, 2016.

(51) Int. Cl.
*G01N 21/64* (2006.01)
*H01J 37/32* (2006.01)
*H05H 1/24* (2006.01)

(52) U.S. Cl.
CPC .... *G01N 21/6428* (2013.01); *H01J 37/32422* (2013.01); *H01J 37/32935* (2013.01); *H05H 1/24* (2013.01); *B81C 2201/0138* (2013.01); *G01N 2021/6439* (2013.01)

(58) Field of Classification Search
CPC ........ G01N 21/6428; G01N 2021/6439; H01J 37/32422; H01J 37/32935; H05H 1/24; B81C 2201/0138
See application file for complete search history.

(56) References Cited

U.S. PATENT DOCUMENTS

| 2005/0205210 | A1* | 9/2005 | Devine | H01L 21/67196 |
| | | | | 156/345.32 |
| 2008/0223522 | A1* | 9/2008 | Kobayashi | H01J 37/32935 |
| | | | | 156/345.25 |
| 2010/0037822 | A1 | 2/2010 | Ishibashi et al. | |
| 2013/0022658 | A1 | 1/2013 | Lee | |
| 2015/0376788 | A1 | 12/2015 | Zhou et al. | |

FOREIGN PATENT DOCUMENTS

WO   WO-2007042017 A1 *  4/2007  ........ H01L 21/67011

OTHER PUBLICATIONS

Translation of WO2007042017A1, Meier, Sven, Apr. 19, 2007 (Year: 2007).*
Choudhury, et al., Fluorophore-Based Sensor for Oxygen Radicals in Processing Plasmas, J. Vac. Sci. Technol. A, 2015, 33(6):061305-1 thru 061305-5.
PCT International Search Report and Written Opinion, PCT/US2017/046768, dated Oct. 27, 2017.

* cited by examiner

*Primary Examiner* — Jill A Warden
*Assistant Examiner* — Henry H Nguyen
(74) *Attorney, Agent, or Firm* — Quarles & Brady LLP

(57) ABSTRACT

The present disclosure provides systems and methods for characterizing the interaction of free radicals with various materials and the use of known interactions to isolate free radical generation from free radical interaction with a target molecule.

18 Claims, 8 Drawing Sheets

METHODS AND SYSTEMS FOR TRANSMISSION AND DETECTION OF FREE RADICALS

CROSS-REFERENCE TO RELATED APPLICATIONS

This application is related to, claims priority to, and incorporated herein by reference in its entirety U.S. Provisional Patent Application 62/374,556, filed Aug. 12, 2016.

STATEMENT REGARDING FEDERALLY FUNDED RESEARCH

This invention was made with government support under CBET1066231 awarded by the National Science Foundation. The government has certain rights in the invention.

BACKGROUND

During semiconductor manufacturing/fabrication processes, thin films that are incorporated into semiconductor devices can be exposed to processing plasmas, which are commonly used for deposition, etching, ashing, sputtering, and/or cleaning of the thin films. Plasmas of this sort can contain free radicals and other active species that interact with the material under processing. These interactions can modify the chemical structure of the materials and can penetrate deep into thin films of the materials. These effects can be desirable in some cases, such as with etching processes, or they can be damaging to thin films, in which case the quality and reliability of the eventual device can be compromises.

A need exists for systems and methods for investigating transmission properties of various free radicals through materials, such as those used in semiconductor devices.

Recent developments in the biological sciences have utilized the interaction of free radicals with biomolecules to investigate the conformational structure of the biomolecules. However, in some cases, the free radical generation process can involve harsh environments that would be unsuitable for the biomolecules being investigated. Additionally, some free radical generation processes can require difficult adjustments to control the amount of free radicals being introduced to the biomolecules being investigated. In some cases, the free radical generation processes can have a minimum free radical generation that exceeds the desired amount of free radicals for interacting with the species of interest.

A need exists for systems and methods for sparing a species being investigated from the potentially harsh environment of free radical generation. A need also exists for systems and methods for reproducibly controlling the properties of the free radicals being introduced to a species of interest.

SUMMARY

The present disclosure overcomes the aforementioned drawbacks by presenting methods and systems relating to transmission and detection of free radicals through thin films.

In an aspect, the present disclosure provides a system including a free radical generation chamber, a free radical source, an interaction chamber, and a free radical transmitting barrier. The free radical source can be positioned within the free radical generation chamber. The free radical source can be configured to generate one or more free radicals. The free radical transmitting barrier can be positioned between the free radical generation chamber and the interaction chamber. The free radical transmitting barrier can include a barrier material having a known response to interaction with the one or more free radicals.

In another aspect, the present disclosure provides a free radical generation device including a free radical source and a free radical transmitting barrier. The free radical source can generate one or more free radicals. The free radical transmitting barrier can be positioned in a direction relative to the free radical source. The free radical source can be configured to emit at least one free radical of the one or more free radicals in a direction of the free radical transmitting barrier and with sufficient velocity to travel through the free radical transmitting barrier.

In a further aspect, the present disclosure provides a kit including a plurality of free radical generation devices and an identifier. The plurality of free radical generation devices can each include a free radical source and a free radical transmitting barrier. The free radical source can generate one or more free radicals. The free radical transmitting barrier can be positioned in a direction relative to the free radical source. The free radical source can be configured to emit at least one free radical of the one or more free radicals in a direction of the free radical transmitting barrier and with sufficient velocity to travel through the free radical transmitting barrier. The free radical sources of at least two of the plurality of free radical generation devices are configured to generate different amounts of free radicals, the free radical transmission barriers of at least two of the plurality of free radical generation devices can have known different free radical transmission properties, or a combination thereof. The identifier can be configured to correlate a specific free radical generation device of the plurality of free radical generation devices with the different amounts of free radicals or the different free radical transmission properties for the specific free radical generation device.

In yet another aspect, the present disclosure provides a kit include a plurality of free radical transmitting barriers and an identifier. The plurality of free radical transmitting barrier can have different known responses to interaction with a free radical species. The identifier can be configured to correlate a specific free radical transmitting barrier of the plurality of free radical transmitting barriers with the known response for the specific free radical transmitting barrier.

In an additional aspects, the present disclosure provides a system including a free radical source, an interaction chamber, and a material mount. The free radical source can be configured to generate a plurality of free radicals. The interaction chamber can include a free radical detection species. The material mount can be configured to receive a material of interest. The material mount can be configured to position the material of interest between the free radical source and the interaction chamber. The free radical detection species can undergo a measurable change in at least one property after interaction with one or more of the plurality of free radicals. At least a portion of the plurality of free radicals can move from the free radical source, through the material of interest when mounted in the material mount, and into the interaction chamber.

In another aspects, the present disclosure provides a method. The method can include one or more of the following steps: a) generating a plurality of free radicals from a free radical source, the free radical source positioned on a first side of a material of interest that is opposite a second side of the material of interest, wherein the plurality of free radicals is moving in a direction toward the material of interest; b) measuring a measurable change in at least one property of a free radical detection species positioned on the second side of the material of interest, the measuring occurring after a length of time where at least a portion of the plurality of free radicals have passed through the material of interest and interacted with the free radical detection species, the free radical detection species undergoing the measurable change in at least one property after interaction with one or more of the plurality of free radicals.

In yet another aspect, the present disclosure provides a method of modifying a target molecule located in a sample. The sample can be located in an interaction chamber positioned on a second side of a free radical transmitting barrier. The method can include one or more of the following steps: a) generating a plurality of free radicals from a free radical source, the free radical source positioned in a free radical generation chamber positioned on a first side of the free radical transmitting barrier that is opposite the second side, wherein the plurality of free radicals is moving in a direction toward the free radical transmitting barrier and the interaction chamber; and b) waiting a length of time sufficient for one or more of the plurality of free radicals to pass through the free radical transmission barrier and interact with the target molecule, thereby modifying the target molecule.

BRIEF DESCRIPTIONS OF THE DRAWINGS

DETAILED DESCRIPTION

Figure 1:
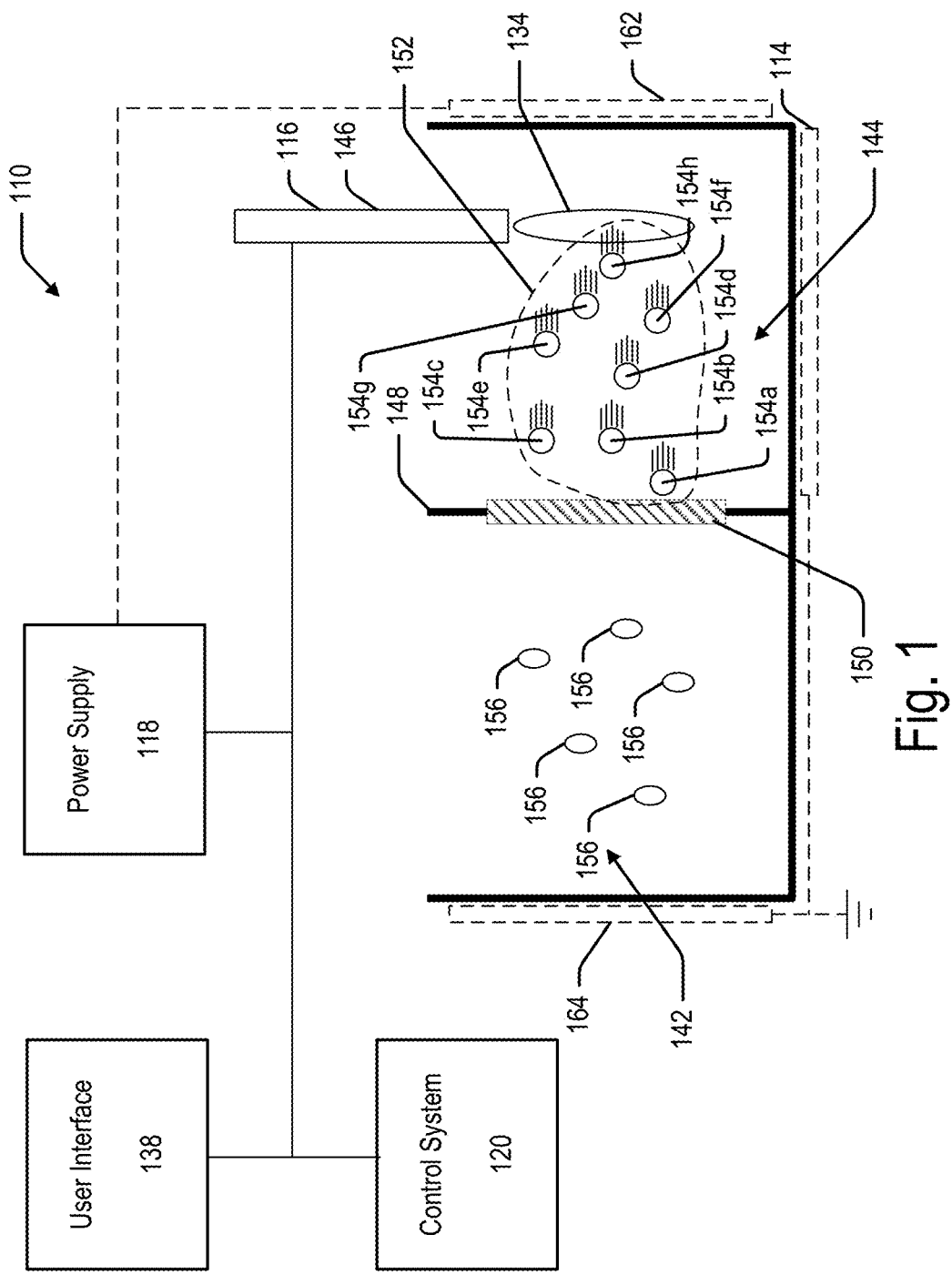
FIG. 1 is a system according to an aspect of the present disclosure.

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices and methods relating to modifying biological molecules are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

As used herein, the term "free radical detection species" is to be interpreted broadly to include any of the following either alone or in combination: 1) a single molecule that has a measurable response to interaction with one or more free radicals—this expressly contemplates atoms, ions, electrons, photons, molecules, compounds, particles, crystalline or amorphous or a combination of structures, fluids, gases, plasmas, biological samples, etc. or combinations thereof that are capable of interacting with a free radical to induce a measurable change (for example, a molecule that has a first shift in fluorescence on interaction with a first free radical and which may or may not undergo additional changes on interaction with subsequent free radicals) and/or atoms, ions, electrons, photons, molecules, compounds, particles, crystalline or amorphous or a combination of structures, fluids, gases, plasmas, biological samples, etc., or combinations thereof that are capable of interacting with multiple free radicals to induce multiple measurable changes (for example, a compound that has a first shift in fluorescence on interaction with a first radical, a second shift in fluorescence on interaction with a second radical, and so on); 2) a plurality of atoms, ions, electrons, photons, molecules, compounds, particles, crystalline or amorphous or a combination of structures, fluids, gases, plasmas, biological samples, etc., or combinations thereof having a collective measurable response to interaction with one or more free radicals; and 3) a plurality of atoms, ions, electrons, photons, molecules, compounds, particles, crystalline or amorphous or a combination of structures, fluids, gases, plasmas, biological samples, etc., or combinations thereof each having a unique measurable response to interaction with one or more free radicals.

The various aspects may be described herein in terms of various functional components and processing steps. It should be appreciated that such components and steps may be realized by any number of hardware components configured to perform the specified functions.

Systems

This disclosure provides systems. The systems can be suitable for use with the methods and kits described herein. When a feature of the present disclosure is described with respect to a given system, that feature is also expressly contemplated as being combinable with the other systems, the methods, and the kits described herein, unless the context clearly dictates otherwise.

Figure 2:
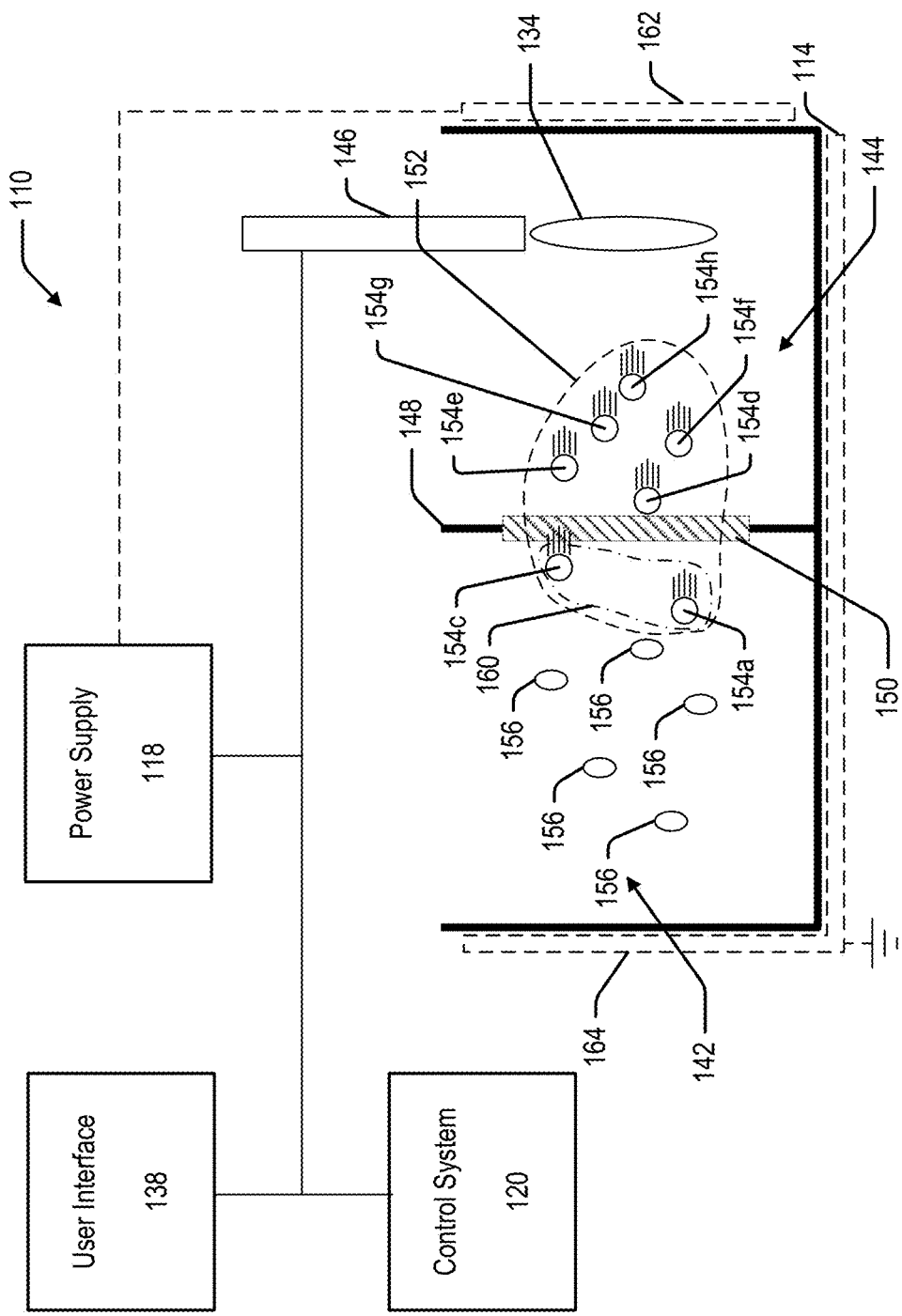
FIG. 2 is a system according to an aspect of the present disclosure.
Figure 3:
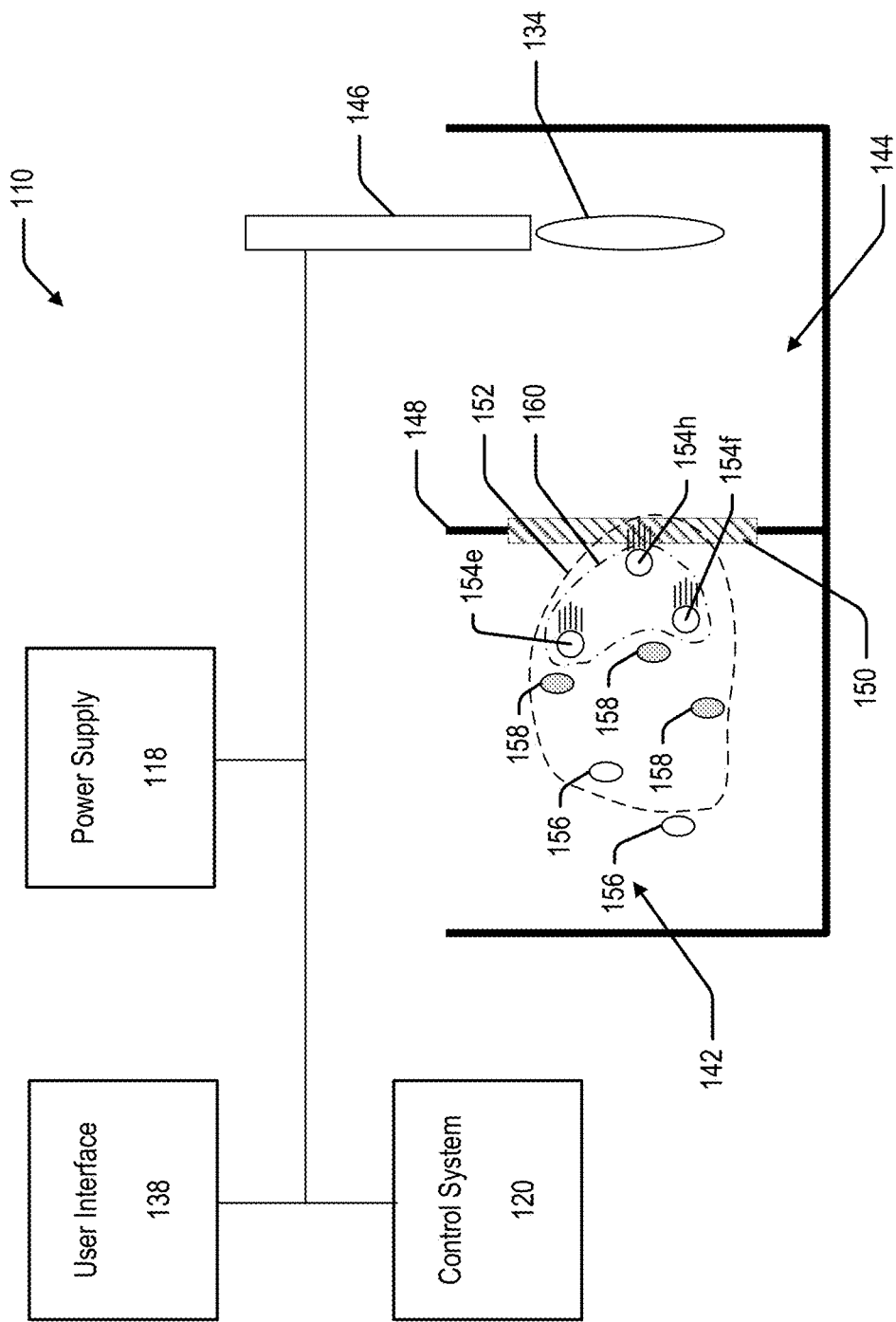
FIG. 3 is a system according to an aspect of the present disclosure.

In an aspect, referring to FIGS. 1 to 3, the disclosure provides a system 110 for measuring the free radical interaction properties of a material of interest 150. The system 110 can include an interaction chamber 142, a free radical generation chamber 144, a free radical source 146, a material mount 148 configured to retain the material of interest 150, a user interface 138, a power supply 118, and a control system 120. The system 110 can optionally include a radical acceleration electrode 162 and a radical acceleration ground electrode 164.

The free radical source 146 is configured to generate a plurality of free radicals 152, where the free radicals 154a, 154b, 154c, 154d, 154e, 154f, 154g, 154h are emitted in the direction of the material of interest 150 and the interaction chamber 142. Note that free radicals not illustrated may be emitted in other directions. The free radical source 146 is configured to generate a known quantity or rate of free radicals to interact with the material of interest. For example, the free radical source 146 can be configured to generate a fixed number of free radicals to interact with the material of interest 150 per a given unit of time.

The interaction chamber 142 can include one or more free radical detection species 156.

FIG. 1 shows a stage of the operation of the system 110 where the plurality of free radicals has yet to encounter the material of interest 150. FIG. 2 shows a stage of operation of the system 110 where some of the plurality of free radicals has encountered the material of interest 150. Free radical 154b was absorbed or otherwise removed from the plurality of free radicals 152 upon interaction with the material of interest 150. FIG. 3 shows a stage of the operation of the system 110 where all of the plurality of free radicals has encountered the material of interest. Free radical 154g was absorbed or otherwise removed from the plurality of free radicals 152 upon interaction with the material of interest 150. Free radicals 154a, 154c, and 154d each interacted with a free radical detection species 156, thus converting the respective free radical detection species 156 into modified free radical detection species 158. In FIGS. 2 and 3, a portion 160 of the plurality of free radicals is transmitted through the material of interest 150 and have not interacted with a free radical detection species. It should be appreciated that some radicals can be absorbed by the material of interest, some may undergo a chemical reaction with the material of interest, some may undergo a physical interaction with the material of interest, and some may be transmitted through the material of interest without any interactions.

Figure 4:
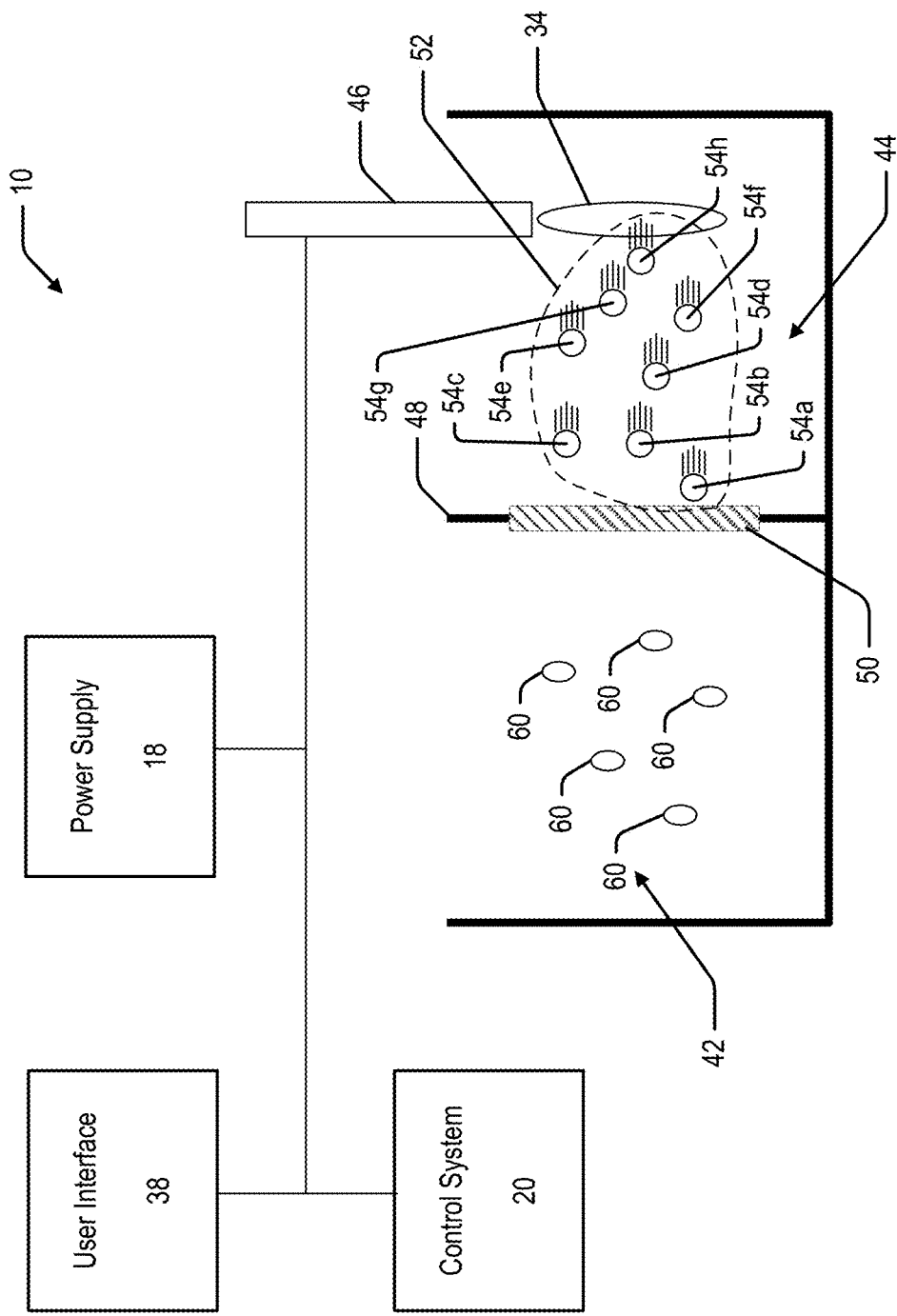
FIG. 4 is a system according to an aspect of the present disclosure.

In certain aspects, referring to FIG. 4, a system 10 for modifying a target molecule 60 can have a configuration similar to the system 110, where one or more target molecules 60 are positioned where the one or more free radical detection species 156 are shown in FIGS. 1-3, and where a free radical transmitting barrier 50 is positioned where the material of interest 150 is shown in FIGS. 1-3. The system 10 can also include an interaction chamber 42, a free radical generation chamber 44, a free radical source 46, an optional free radical transmitting barrier mount 48, a user interface 38, a power supply 118, and a control system 120.

Figure 5:
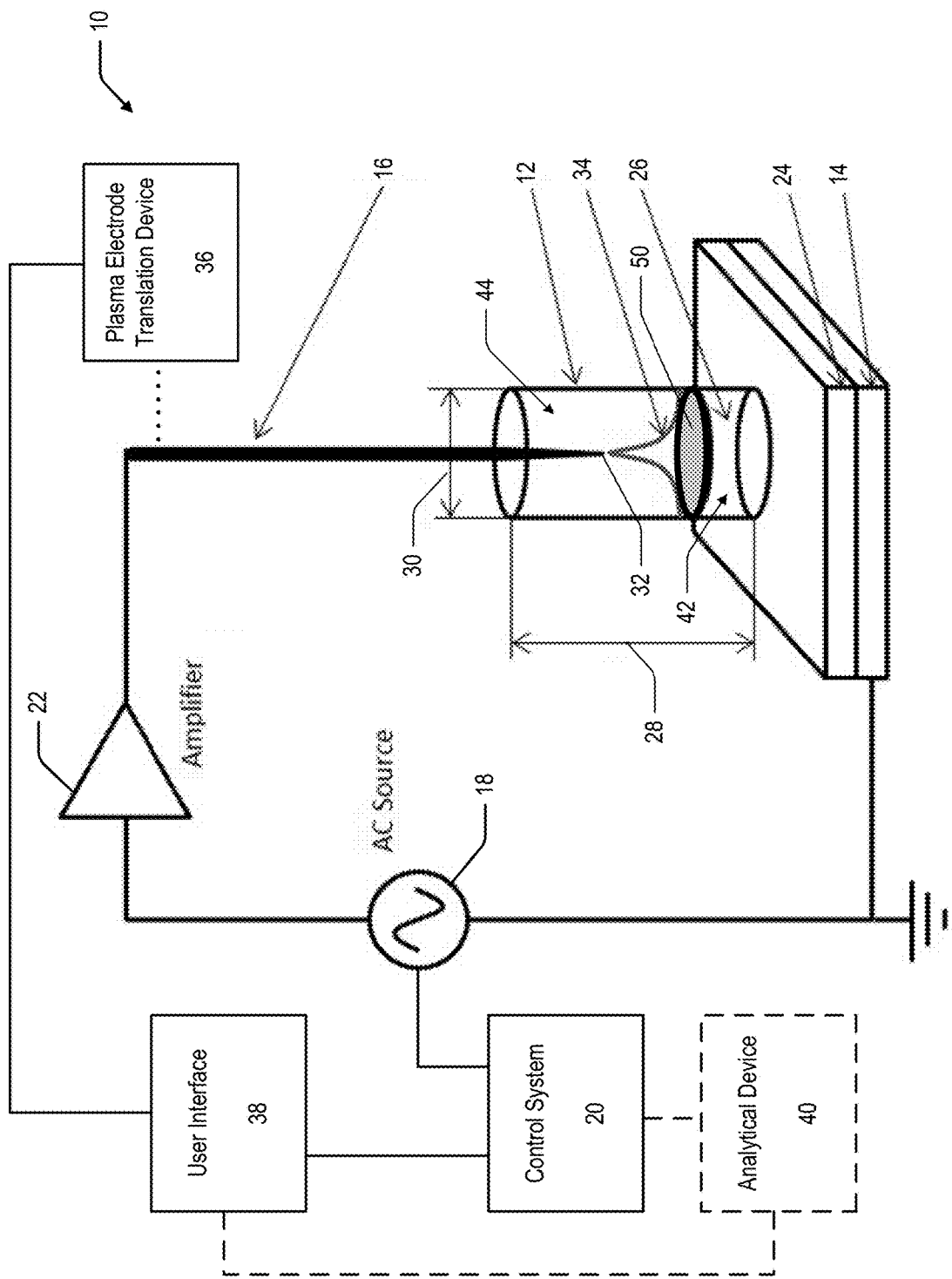
FIG. 5 is a system according to an aspect of the present disclosure.

In an aspect, referring to FIG. 5, the disclosure provide a system 10 for modifying a target molecule or atom 60 with free radicals and isolating, shielding, and/or protecting the target molecules from the region of generation of the free radicals, and/or otherwise preventing interaction between the generation of the free radicals and the target molecules. One specific arrangement of the system 10 is described below, but various modifications are possible. For example, the sample chamber 12 can split into an interaction chamber 42 that contains the target molecules 60 within a sample 26, a free radical generation chamber 44, and the interaction chamber 42 and the free radical generation chamber 44 can be separated by a free radical transmitting barrier 50. It should be appreciated that aspects of the disclosure described below with respect to a sample chamber 12 are applicable to an interaction chamber that contains target molecules 60 with a sample 26, a free radical generation chamber 44, and a free radical transmitting barrier 50 separating the interaction chamber 42 and the free radical generation chamber.

In an aspect, referring to FIG. 5, the disclosure provides a system 10 for modifying a biological molecule with one or more free radicals generated by a plasma. The system 10 for modifying a biological molecule can include a sample chamber 12, a ground electrode 14, a plasma electrode 16, a power supply 18, and a control system 20. The system 10 can also include an amplifier 22 located between the power supply 18 and the plasma electrode 16. The system can include a dielectric 24 located between the sample chamber 12 and the ground electrode 14.

The free radical source 46, 146 can be but is not limited to being a plasma source that generates one or more free radicals via a plasma, such as a plasma electrode 16, 116 and ground electrode 14, 114 coupled to the appropriate electronics for generating a plasma 34, or generated by laser photolysis, chemical reactions, radiation-based generation, thermal generation of radicals, etc., or a combination thereof. In certain cases, the free radical source 46, 146 can be a plasma jet. As used herein, the term "plasma jet" refers to a device that generates a plasma within a first space and propels the generated plasma toward a target by way of movement of a gas and the shaping of the plasma jet.

The free radical generation chamber 44, 144 can be configured to retain a liquid, a gas, a plasma, or a vacuum.

The interaction chamber 42, 142 can be configured to retain a liquid, a gas, a plasma, or a vacuum.

The target molecules 60 can be selected from the group consisting of biological molecules (as described in greater detail below), organic and inorganic molecules, atoms, etc., and combinations thereof. The target molecules 60 can be in a liquid and/or gas phase.

The free radical detection species 156 can be selected from the group consisting of a fluorophore, such as an Alexa Fluor™ fluorophore available commercially from ThermoFisher Scientific, Waltham, Mass., a green fluorescent protein; a specifically non-fluorescent protein, such as cytochrome c, bovine serum albumin, or the like; a small molecule, such as coumarin, terephthalic acid, and the like; combinations thereof; and the like having a molecular structure where interaction with a free radical modifies a property. The property can be selected from the fluorescence properties of the free radical detection species 156; laser-induced fluorescence properties of the free radical detection species 156; chemical reaction properties of the free radical detection species 156; infrared spectroscopy (such as Fourier transform infrared spectroscopy) properties of the free radical detection species 156; x-ray photoelectron spectroscopy properties of the free radical detection species 156; mass spectrometry properties of the free radical detection species 156; combinations thereof; and the like. In certain aspects, the radical detection species 156 can detect the presence of the radical via N addition. In certain aspects, the radical detection may take place directly or indirectly by observing the reaction products of the reaction between the radical and material species, such as with atoms, ions, electrons, photons, molecules, compounds, particles, crystalline or amorphous or a combination of structures, fluids, gases, plasmas, biological samples, etc.

The sample chamber 12 and/or the interaction chamber 42, 142 can be configured to receive a sample 26. The sample 26 can be those described elsewhere herein. The sample chamber 12, the plasma generation chamber 44, 144, and/or the interaction chamber 42, 142 can have an inner surface that is chemically and/or biologically inert. As used herein, chemically inert refers to a material not impacting the chemical structure of one or more biological molecules or target molecules. As used herein, biologically inert refers to a material not impacting the conformational state of one or more biological molecules or target molecules.

The sample chamber 12 and/or the interaction chamber 42, 142 can take various shapes, such as a cylinder, an elliptical cylinder, a cuboid, a frustum of a cone, a frustum of a pyramid (triangular, rectangular, pentagonal, etc.), a prism (triangular, pentagonal, hexagonal, etc.), any suitable shape for holding a gaseous or liquid sample, any subdivision thereof (for example, a semicylinder), and the like.

The sample chamber 12 can have a height 28 and a width 30 that are configured to provide optimal plasma generation, and subsequent interaction of generated radicals. The height 28 can be 0.75 inches and the width 30 can be 0.5 inches, though other sizes of sample chamber 12 are contemplated and appropriate sizes can be determined by a person having ordinary skill in the art.

In some aspects, the sample chamber 12, the plasma generation chamber 44, 144, and/or the interaction chamber 42, 142 can have an open top. In some aspects, the sample chamber 12, the plasma generation chamber 44, 144, and/or the interaction chamber 42, 142 can have a closed top. In aspects where the sample chamber 12 has a closed top, the sample 26 can entirely fill the sample chamber 12, such that there is no fluid, such as a gas, air, etc., contacting the sample 26 or the sample 26 can fill a portion of the sample chamber 12 with a fluid occupying the remaining portion of the sample chamber 12. The sample chamber 12, if having an open top, may be placed in a gas or vacuum environment as appropriate.

In certain aspects, the sample chamber 12 and/or the interaction chamber 42, 142 can be a portion of a microfluidic device and/or channel.

The material of interest 150 can be a thin film. The free radical transmitting barrier 50 can be a thin film. Either thin film can be freestanding. A freestanding thin film can have a thickness of between 1 nm and 5 cm, including but not limited to, a thickness of between 10 nm and 1 cm, or between 50 nm and 500 nm. Either thin film can be mounted on a substrate. The substrate can have a thickness of between 1 nm and 10 cm, including but not limited to, a thickness of between 1 μm and 1 mm, or between 10 μm and 1 mm. Either thin film can include multiple layers. The substrate can be used as a mechanical support for the material of interest 150 or the free radical transmitting barrier 50, thus improving mechanical properties. The substrate can be freestanding. In some cases, the substrate can allow for the transmission of free radicals. The substrate can comprise a substrate material selected from the group consisting of silicon nitride, silicon dioxide, silicon oxynitride, hafnium oxide, silicon carbide, silicon carbon nitride, silicon carbon hydroxide, and combinations thereof. In certain aspects, the substrate material can be a low-k or high-k dielectric. In certain aspects, the substrate material can be a semiconductor material.

A free radical transmitting barrier 50 can be composed of a barrier material having a known or unknown response to interaction with the free radicals 54*a-h* being utilized. Examples of suitable barrier materials for use in the free radical transmitting barrier can include, but are not limited to, metal oxides, such as SiN, $SiO_2$, SiCOH, $HfO_2$, $Ta_2O_5$, and the like; polymers; amorphous materials; crystalline materials; biologically-derived membranes; capillary windows; mesoporous and/or nanoporous materials; and the like. It should be appreciated that the present disclosure contemplates the use of materials that have not yet been determined to have a known response to the free radicals 54*a-h* being utilized, but is intended to cover materials having the necessary properties as described herein. In some aspects, one or more of the methods discussed below can be utilized to determine the known response of the materials to the free radicals 54*a-h* being utilized.

The barrier material and/or the substrate can be mesoporous and/or nanoporous. The mesoporous and/or nanoporous barrier material and/or substrate can have pores with an average pore size of between 0.1 nm and 100 nm, including but not limited to, an average pore size of between 1 nm and 75 nm, or between 5 nm and 50 nm. The pore size can be determined using several techniques. One of the most commonly used techniques to determine the pore sizes in thin solid films is ellipsometric porosimetry. The mesoporous and/or nanoporous barrier material and/or substrate can be used as a size-selective means to isolate free radicals 54*a-h* of a preselected size.

In aspects where free radical generation is achieved via a plasma 34, 134, the free radical transmitting barrier 50, 150 can be configured to isolate the plasma 34, 134 in the free radical generation chamber 44, 144 and prevent the plasma 34, 134 from entering the interaction chamber 42, 142 and/or from interacting with the target molecules 60. A similar design may be used to separate the generation chamber from the interaction chamber using other methods for radical generation.

The ground electrode 14, 114 can be composed of a conductive material known to those having ordinary skill in the art. Examples of suitable conductive materials for use in the ground electrode 14, 114 include, but are not limited to, copper, silver, gold, aluminum, iron, graphite, calcium, beryllium, magnesium, rhodium, molybdenum, iridium, tungsten, zinc, cobalt, cadmium, nickel, ruthenium, lithium, osmium, platinum, palladium, selenium, tantalum, columbium, lead, vanadium, tin, titanium, conductive oxides thereof, conductive alloys thereof, conductive polymers, and combinations thereof.

The plasma electrode 16 can be composed of a conductive material known to those having ordinary skill in the art. Examples of suitable conductive materials for use in the plasma electrode 16 include, but are not limited to, the materials listed above as suitable for use in the ground electrode 14, 114.

In some aspects, the plasma electrode 16 can be in close proximity to the sample or can contact the sample. In cases where the plasma electrode 16 is in close proximity to the sample or in contact with the sample, the plasma electrode 16 can be made of a material that is non-contaminating of the sample. A person having ordinary skill in the art will appreciate that the extent to which the plasma electrode 16 is contaminating of the sample is dependent on the properties of the sample. The plasma electrode 16 can be non-contaminating to the samples described elsewhere herein.

The plasma electrode 16 can have a plasma source point 32 that is the point from which the plasma 34 emerges. The plasma electrode 16 can have multiple plasma source points 32.

In certain aspects, the plasma electrode 16 can have a dielectric coating (not illustrated). The dielectric coating can cover at least the plasma source point 32. A person having ordinary skill in the art will appreciate the impact that such a coating might have on the plasma generation properties of the system 10, and can adjust the various aspects of the system 10 to accommodate such a coating while maintaining the overall performance of the system 10.

In certain aspects, the plasma electrode 16 can have the shape of a needle or any shape suitable for producing a plasma 34. The plasma source point 32 can take a shape that is suitable for producing a plasma 34 in accordance with the present disclosure. In certain aspects, the plasma source point 32 can take the shape of a needle tip, a convex rounded surface, a flat surface, multiple needle tips, a disk, a sphere, or other shapes known to a person having ordinary skill in the art to be suitable for generating a plasma 34.

In certain aspects, the plasma 34 can be generated by a plasma generator that does not include electrodes. As one example, a microwave source can be configured to generate a plasma 34 having the properties described elsewhere herein.

In certain aspects, the plasma electrode 16 can be mechanically coupled to a plasma electrode translation device 36. Examples of plasma electrode translation devices 36 include, but are not limited to, 1-, 2-, or 3-dimensional translation stages (manual and motor-driven), a robotic arm, an array of electrodes, and the like.

Also contemplated are systems where the sample chamber 12, the ground electrode 14, 114, and optionally the dielectric 24 are movable relative to the plasma electrode 16 by way of a sample chamber translation device (not illustrated). Examples of sample chamber translation devices include those described above with respect to the plasma electrode translation devices 36.

The control system 20 can include various function generators, programmable controls, pulse generators, voltmeters, ammeters, light sensors, thermometers, gas pressure sensors, gas flow controllers, fluorometers, monochromators, liquid-flow meters, liquid-flow controllers, timers, or other components that a person having ordinary skill in the art would recognize as useful for the control of various components of the system 10.

The system 10 can include a user interface 38. The user interface 38 can be in communication with the control system 20 and/or the electrode translation device 36. The user interface can take the form of a computer, a personal device, such as a tablet or a smart phone, an arrangement of mechanical inputs such as buttons, knobs, switches, and the like, or other means of receiving user input and providing signals to the control system 20 and/or the electrode translation device 36 to operate the system 10. The spacing of the electrodes used to generate a plasma can be made adjustable as well as the frequency and magnitude of the voltage placed across the electrodes.

In certain aspects, the system 10 can have more than one sample chamber 12. In these aspects, the system 10 can also have more than one plasma electrode 16 in an amount equal to the number of sample chambers 16. For example, the system 10 can have an array of sample chambers 12 similar to a 96-well plate and an array of individual or independent plasma electrodes 16 configured such that each sample chamber 12 has a plasma source point 32 positioned within it for generation of plasmas 34.

Figure 8:
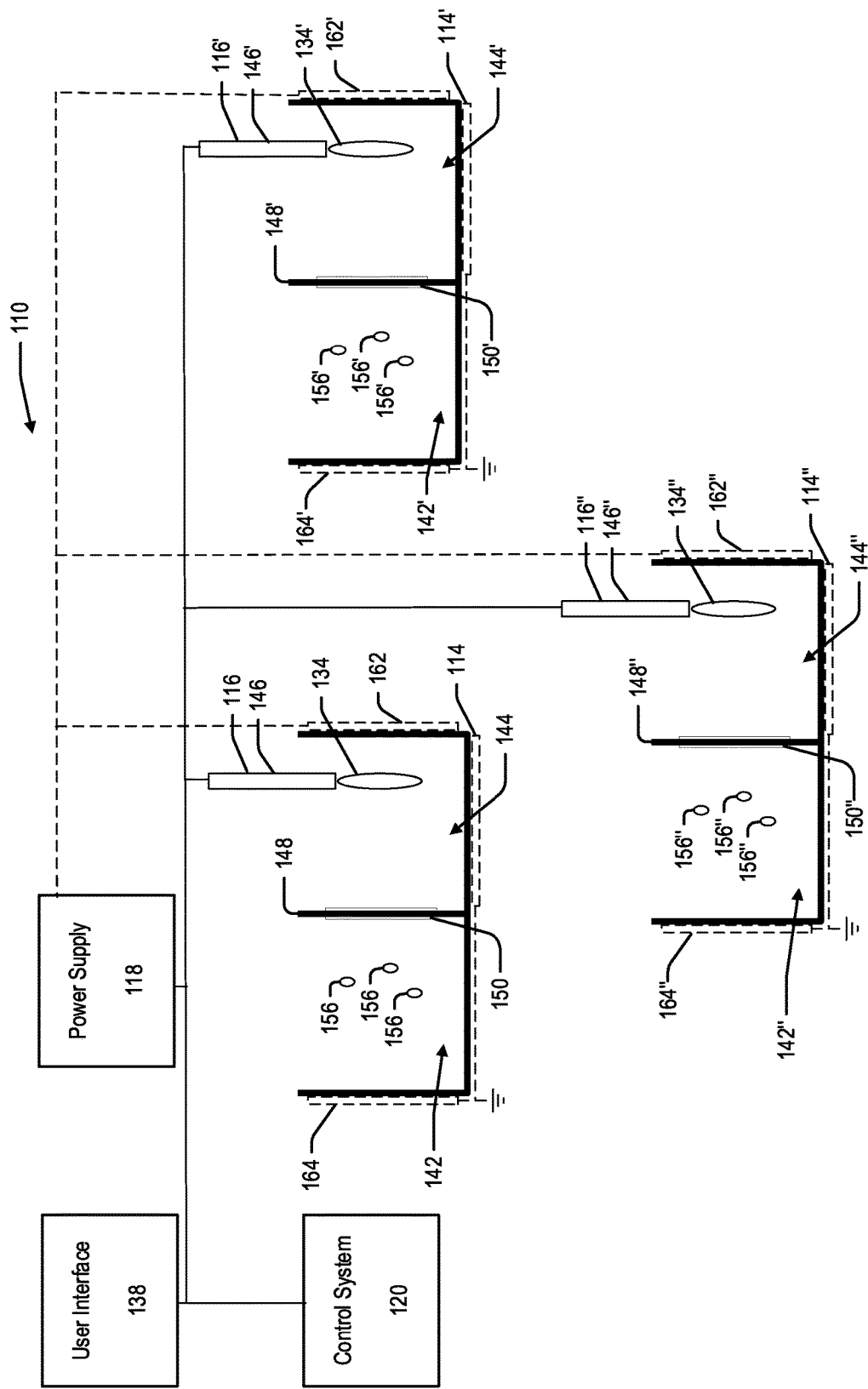
FIG. 8 is a system according to an aspect of the present disclosure.

"Referring to FIG. 8, in certain aspects, the system 10, 110, can have more than one free radical generation chamber 44, 144, 144',144" (i.e., additional free radical generation chambers), each comprising a free radical source 46 146, 146',146" (i.e., additional free radical sources). In certain aspects, the system 10, 110 can have more than one interaction chamber 42, 142, 142',142" (i.e., additional free radical interaction chambers). In certain aspects, the system 10,110 can have more than one material mount 48, 148, 148',148" (i.e., additional material mounts) configured to hold additional materials of interest 50, 150, 150',150". The additional material mounts can be positioned between at least one free radical source 46, 146, 146',146" and at least one interaction chamber 42, 142, 144',144". In certain aspects, the system 10, 110 can have more than one free radical detection species 60, 156, 156',156" (i.e., additional free radical detection species)."

In an aspect, the system 10 can be used for assessing a sample. The system 10 for assessing the sample can optionally include an analytical device 40 capable of determining whether a portion of a target molecule 60 or a biological molecule has been modified by a radical. The analytical device 40 can optionally be in electronic communication with the control system 20 and/or the user input 38. The control system 20 can optionally coordinate control of the analytical device 40 along with other aspects of the system 10. The user interface 38 can optionally be used in coordination with the analytical device 40 to control the analytical device and/or to directly receive user inputs for control of the analytical device 40.

In certain aspects, the analytical device 40 can measure the material, electrical, chemical, mechanical, or structural properties. More than one analytical device 40 can be utilized. In certain aspects, the analytical device 40 can be a fluorometer, a mass spectrometer, a multimeter configured to measure a resistance, capacitance, or other electrical property, a device to analyze mechanical properties, such as a nanoindenter, NMR, XASS, XRD, FTIR, XPS, XRR, ESR, Laser induced Fluorescence, optical spectrometry, mass spectrometry or the like. The fluorometer can be a dedicated fluorometer configured to detect species of particular relevance that can be modified by the free radical, such as free radical modified fluorophores. The mass spectrometer can be a dedicated mass spectrometer configured to detect species of particular relevance. For example, a dedicated mass spectrometer can be configured to detect the mass of oxidized and non-oxidized peptides, for which sequence information localizing the modified amino acids can be obtained, while ignoring other masses.

In certain aspects, the sample chamber 12 can be directly connected to the analytical device 40, so the sample can be processed automatically without requiring a user to transfer the sample to the analytical device. In certain aspects, an automated transfer can occur by way of, for example, a robotic pipette system.

In certain aspects, the system 10 can include a sample hopper for automatically introducing the sample 26 into the sample chamber 12. An example of a sample hopper includes, but is not limited to, an automated pipette positioned above the sample chamber. A person having ordinary skill in the art will appreciate that automation technology that is usable with other technologies, such as gas chromatography, can be usable with the system 10.

By using the automated loading and/or the automated transfer to the analytical device, the system 10 can automatically optimize the operational parameters. For example, the system 10 could have stored in a memory a reference fluorescence spectrum or mass spectrum. The system could then automatically introduce a reference sample into the sample chamber, automatically oxidize the reference sample with a set of operational parameters, automatically transfer the oxidized reference sample to a fluorimeter or mass spectrometer, automatically acquire a fluorescence or mass spectrum of the reference sample, the compare the acquired fluorescence or mass spectrum with the stored reference fluorescence or mass spectrum. The system could repeat this process and vary the operational parameters using an optimizing routine until the acquired fluorescence or mass spectrum substantially matches the stored reference fluorescence or mass spectrum.

Referring to FIGS. 1 and 2, an optional aspect of the system 110 is illustrated, where the free radical source 146 includes a plasma electrode 116 and a ground electrode 114, and the system 110 includes a radical acceleration electrode 162 and a radical acceleration ground electrode 164. In the illustrated aspect of FIG. 1, the ground electrode 114 and the radical acceleration ground electrode 164 are separate and distinct electrodes. In the illustrated aspect of FIG. 2, the ground electrode 114 and the radical acceleration ground electrode 164 are a single electrode. Application of a voltage across the radical acceleration electrode 162 and the radical acceleration ground electrode 164 can accelerate the free radicals 154a, 154b, 154c, 154d, 154e, 154f, 154g, 154h.

As used herein, a "ground electrode" refers to an individual ground electrode or a plurality of ground electrodes that grounded substantially equivalently to one another. For example, a plurality of copper electrodes that are all electronically connected to a single ground can be considered a ground electrode in the context of this disclosure. For clarity, reference to a ground electrode includes any number of individual ground electrodes.

Methods

This disclosure also provides a variety of methods. It should be appreciated that various methods are suitable for use with the other methods described herein. Similarly, it should be appreciated that various methods are suitable for use with the systems and kits described elsewhere herein. When a feature of the present disclosure is described with respect to a given method, that feature is also expressly contemplated as being useful for the other methods, the systems, and the compositions described herein, unless the context clearly dictates otherwise.

The methods of the present disclosure generally emerge from a discovery of a system and method that allow the generation of free radicals, the transmission of free radicals through a material of interest, the detection of those free radicals, and the determination of properties of the material of interest by way of the information gained from the detection of the free radicals.

In one aspect, this disclosure provides a first method that generally involves the following steps: a) generating a plurality of free radicals; and b) measuring a measurable change at least one free radical detection species or system that is positioned to interact with the at least a portion of the plurality of free radicals after the at least a portion of the plurality of free radicals have passed through the material of interest. More specifically, the method can include: a) generating a plurality of free radicals from a free radical source, the free radical source positioned on a first side of a material of interest that is opposite a second side of the material of interest, wherein at least a portion of the plurality of free radicals is moving in a direction toward the material of interest; b) measuring a measurable change in at least one property of a free radical detection species or system positioned on the second side of the material of interest, the measuring occurring after a length of time where at least a portion of the plurality of free radicals have passed through the material of interest and interacted with the free radical detection species, the free radical detection species or system having the measurable change in at least one property after interaction with one or more of the plurality of free radicals.

In certain aspects, the measurable change in the at least one property of the free radical detection species can be proportional to an amount of free radicals interacting with the free radical detection species. In certain aspects, the method can further include characterizing one or more properties of the material of interest using the measurable change in the at least one property of the free radical detection species or system. In certain aspects, the method can result in the production of desired changes to the material which can be detected using some or all of the systems described here. In certain aspects, the at least one property can be a fluorescence response. The fluorescence response can be selected from the group consisting of a fluorescence intensity, a fluorescence spectrum shape, a fluorescence wavelength, combinations thereof, and the like.

In another aspects, this disclosure provides a second method that generally involves the following steps: a) generating a plurality of free radicals; b) waiting a length of time for at least a portion of the plurality of free radicals to pass through a material of interest and interact with a target molecule. More specifically, the method can include: a) generating a plurality of free radicals from a free radical source, the free radical source positioned in a free radical generation chamber positioned on a first side of the free radical transmitting barrier that is opposite the second side, wherein the plurality of free radicals is moving in a direction toward the free radical transmitting barrier and the interaction chamber; and b) waiting a length of time sufficient for one or more of the plurality of free radicals to pass through the free radical transmission barrier and interact with the target molecule, thereby modifying the target molecule.

In certain aspects, the generating a plurality of free radicals can include generating a plasma.

The generating a plasma of step a) can thereby convert one or more of a plurality of radical precursors into one or more radicals. Examples of the radical include, but are not limited to, a hydroxyl radical (.OH), a hydrogen radical (H.), a nitrite or nitrogen dioxide radical (.$NO_2$), a nitrate radical (.$NO_3$), a peroxide radical (.OOH), other radicals known to those having ordinary skill in the art as being generated by a plasma interacting with a radical precursor, combinations thereof, and the like. Examples of the radical precursor include, but are not limited to, a hydroxyl radical precursor, such as water or hydrogen peroxide, a hydrogen radical precursors, such as hydrogen gas, a nitrite or nitrogen dioxide radical precursor, such as nitrite or nitrogen dioxide, a nitrate radical precursor, such as nitrate, a peroxide radical precursor, such as hydrogen peroxide, other precursors known to those having ordinary skill in the art to be converted into a radical by interacting with a plasma, combinations thereof, and the like. The length of time can be a length of time sufficient for the one or more radicals to pass through the material of interest 50 and interact with the free radical detection species or system 156 or to pass through the free radical transmitting barrier and interact with the target molecule 60, biological molecule, or detection system. This interaction can modify the free radical detection species 156, the target molecule 60, or the biological molecule.

In the generating a plasma step, a plurality of charged radicals can be generated (as opposed to the neutral free radicals described elsewhere), accelerated, and then neutralized. The charged radicals can be accelerated using techniques known in the mass spectrometric arts (such as charging a plate with the necessary charge to accelerate charged particles in a desired direction). The charged radicals can be passed through a neutralization material, such as a flow of sulfur hexafluoride gas, in order to neutralize the radicals without impacting their radical nature.

The generating a plasma step can include generating a single plasma pulse, a sequence of plasma pulses, or a continuous plasma discharge.

In certain aspects, the plasma can be generated by a voltage of between 1 V and 1 GV, including but not limited to, a voltage of between 500 V and 100 kV, between 1 kV and 50 kV, or between 5 kV and 500 kV. As with the distances disclosed above, these voltages can be scaled up or down depending on the specific operational parameters.

In certain aspects, the plasma can be generated by multiple pulses whose duty cycles, repetition rate and amplitude can be varied by someone skilled in the art to ensure that the production rate and lifetime of radicals is optimized and to minimize the maximum temperature rise of the gas or liquid in the radical generation system.

In certain aspects, the radical generation system may be cooled to remove excess heat. The cooling system may be but not limited to a liquid nitrogen bath or liquid nitrogen vapor bath, a refrigeration system, a Peltier cooling system, or a water cooling system.

In aspects utilizing a sequence of plasma pulses, the operational parameters in this paragraph can be utilized. The plasma pulses can have a pulse width in a range of between 1 ps and 1 ms, including but not limited to, a pulse with in a range of between 500 ps and 100 µs or between 1 ns and 10 µs. The sequence of plasma pulses can have a frequency in a range of between 1 Hz and 100 GHz, including but not limited to, a frequency in a range of between 100 Hz and 100 MHz, or between 1 kHz and 1 MHz. The sequence of plasma pulses can be generated for a total length of time in a range of between 1 ns and hours to days, including but not limited to, a total length of time in a range of between 100 ns and 20 minutes, between 1 µs and 1 hour, between 1 ms and 30 minutes, between 1 s and 10 minutes, or between 30 s and 5 minutes. The aforementioned pulse width, frequency, and total length of time parameters for a sequence of plasma pulses can vary depending on the lifetime of the radicals being produced, the properties of the material of interest or the free radical transmitting barrier, the concentration of the free radical detection species, the target molecules, or the target biological molecule, the size of the free radical detection species, the target molecules, or the target biological molecule, the concentration of the radical precursor, the stability of the free radical detection species, the target molecules, or the target biological molecule in the presence of varying concentrations of the radicals, and/or the extent of modification and/or destruction of the free radical detection species, the target molecules, or the biological molecule that is desired.

In certain aspects, the plasma generating step can be configured to generate a concentration of radicals within the sample. In certain aspects, the generating a plasma step can be configured to provide a peak concentration of radicals in the sample that can be between 50 nM and 800 µM, including but not limited to, a peak concentration of radicals in the sample of between 500 nM and 800 nM, between 5 µM and 8 µM, or between 50 µm and 80 µm. In certain aspects, the generating a plasma step can be configured to provide an average concentration of radicals in the sample of between 50 nM and 800 µM, including but not limited to, a peak concentration of radicals in the sample of between 500 nM and 800 nM, between 5 µM and 8 µM, or between 50 µm and 80 µm. In certain aspects, the average concentration can be a fraction or percentage of the values provided based on the "on" time of the plasma, including but not limited to, 75%, 50%, 40%, 30%, 20%, or 10% of the values provided. The average concentration can be measured for the length of time during which the plasma or the sequence of plasma pulses is generated plus a length of time of about 5 seconds, 10 seconds, 30 second, or 1 minute.

In certain aspects, the generating a plasma step can elevate a temperature of the sample by an amount less than an amount that would begin denaturation of the biological molecule or the plurality of biological molecules. If the plurality of biological molecules have different temperatures at which they denature, then the generating a plasma step can elevate the temperature of the sample by an amount less than an amount that would begin denaturation of the biological molecule having the lowest denaturation temperature. For purposes of this aspect of the disclosure, denaturation can refer to denaturation of quaternary, tertiary, or secondary structure.

In certain aspects, the generating a plasma step can elevate a temperature of the sample by less than 200° C., including but not limited to, less than 5° C., or less than 0.5° C. In certain aspects, the generating a plasma step can elevate a temperature of the sample to a temperature of less than 200° C., including but not limited to, a temperature of less than 28.5° C., or a temperature of less than 23.5° C.

In certain aspects, the method can be performed on a sample having a volume of between 1 µL and 400 L, including but not limited to, a volume of between 10 µL and 100 mL, or a volume between 50 µL and 200 µL. Other values for volume outside the disclosed ranges may be suitable in certain circumstances.

The methods of modifying a target molecule or a biological molecule can be extended to modify a plurality of target molecules or biological molecules. This can be done in at least two ways. First, a single sample can contain multiple target molecules or biological molecules. Second, a plurality of samples, each containing at least one target molecule or biological molecule, can undergo the methods described herein. For this second approach involving a plurality of samples, the aspects of the methods described with respect to a single sample, such as volume for example, can be applicable to each of the plurality of samples.

The sample can be a biological sample that contains within it one or more biological molecules or the sample can be a sample that is prepared to include the biological molecule, such as a protein sample that is dissolved in a buffer solution.

In certain aspects, the biological molecule can be selected from the group consisting of a nucleic acid molecule, a protein, a lipid, a biological metabolite, and combinations thereof.

In certain aspects, the sample can be selected from the group consisting of blood, blood plasma, urine, saliva, lymph, tears, sweat, cerebrospinal fluid, amniotic fluid, aqueous humour, vitreous humour, bile, breast milk, cerumen, chyle, chime, endolymph, perilymph, exudates, feces, female ejaculate, gastric acid, gastric juice, mucus, pericardial fluid, peritoneal fluid, pleural fluid, pus, rheum, sebum, serious fluid, semen, smegma, sputum, synovial fluid, vaginal secretion, vomit, living bacterial cultures, living tissue or eukaryotic cell cultures, and combinations thereof. In certain aspects, the sample can be selected from the group consisting of eukaryotic intracellular fluid, eukaryotic extracellular fluid, prokaryotic intracellular fluid, prokaryotic extracellular fluid, homogenized tissue or cells, homogenized tissue or cell culture, homogenized plant tissue, and combinations thereof. In certain aspects where the sample is extracellular fluid, the extracellular fluid can be selected from the group consisting of intravascular fluid, interstitial fluid, lymphatic fluid, transcellular fluid, plant apoplastic or vascular fluid, excess nutrient medium from prokaryotic or eukaryotic in vitro growth, and combinations thereof. In certain aspects where the sample is living bacterial, tissue, or eukaryotic cell cultures, the cultures can be any species of prokaryotic organism, any mammalian tissue or cell culture, any culturable species of eukaryotic organism, or combinations thereof. In certain aspects, the sample can be any living organism or sub-component of an organism, such as one or more cells, that can be suitable positioned in the systems described herein and/or suitable for use in the methods described herein.

In certain aspects, the sample can comprise one or more biological molecules and a buffer solution. In certain aspects, the buffer solution can include or be a phosphate buffered saline solution, tris(hydroxymethyl)aminomethane (tris), tris hydrochloric acid, ammonium bicarbonate, 4-(2-hydroxyethyl)-1-piperazineethanesulfonic acid (HEPES), 3-(N-morpholino)propanesulfonic acid (MOPS), 2-(N-morpholino)ethanesulfonic acid (MES), 2,2-Bis(hydroxymethyl)-2,2',2''-nitrilotriethanol (bis-tris), N-(2-Acetamido) iminodiacetic acid (ADA), piperazine-N,N'-bis(2-ethanesulfonic acid) (PIPES), N-(2-Acetamido)-2-aminoethanesulfonic acid (ACES), 3-(N-morpholinyl)-2-hydroxypropanesulfonic acid sodium salt (MOPSO), 1,3-bis(tris(hydroxymethyl)methylamino)propane (bis-tris propane), N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 3-(Bis(2-hydroxyethyl)amino)-2-hydroxypropane-1-sulfonic acid (DIPSO), 3-[[1,3-dihydroxy-2-(hydroxymethyl)propan-2-yl]amino]-2-hydroxypropane-1-sulfonic acid (TAPSO), Trizma, piperazine-1,4-bis(2-hydroxypropanesulfonic acid) dihydrate (POPSO), 3-[4-(2-Hydroxyethyl)-1-piperazinyl]propanesulfonic acid (HEPPS), N-(2-Hydroxy-1,1-bis(hydroxymethyl)ethyl)glycine (TRICINE), glycylglycine (GLY-GLY), 2-(Bis(2-hydroxyethyl)amino)acetic acid (BICINE), N-(2-hydroxyethyl)piperazine-N'-(4-butanesulfonic acid) (HEPBS), 3-[[1,3-dihydroxy-2-(hydroxymethyl)propan-2-yl]amino]propane-1-sulfonic acid (TAPS), 2-amino-2-methyl-1,3-propanediol (AMPD), N-(1,1-Dimethyl-2-hydroxyethyl)-3-amino-2-hydroxypropanesulfonic acid (AMPSO), N-cyclohexyl-2-aminoethanesulfonic acid (CHES), N-cyclohexyl-2-hydroxyl-3-aminopropanesulfonic acid (CAPSO), 1-amino-2-methyl-1-propanol (AMP), N-cyclohexyl-3-aminopropanesulfonic acid (CAPS), 4-(cyclohexylamino)-1-butanesulfonic acid (CABS), Lysogeny broth (LB) or other nutrient growth media, anything defined as a 'biological buffer', a biologically or physiologically-relevant salt, combinations thereof, and the like. In certain aspects, the buffer solution can have a pH value of between 1 and 14, including but not limited to, a pH of between 3 and 9, or a pH of between 4 and 8.

The operational parameters of the methods described above can be utilized by a person having ordinary skill in the art to introduce a desired amount of oxidation to a target molecule or a biological molecule. In addition, the operational parameters can be utilized by a person having ordinary skill in the art to induce this oxidation with a minimal amount of damage to the target molecule or the biological molecule. On the other hand, the operational parameters can be utilized by a person having ordinary skill in the art to induce this oxidation under conditions that cause a desired amount of damage to the target molecule or the biological molecule. It should be appreciated that various sorts of information can be realized from methods that induce no damage and various different sorts of information can be realized from methods that induce controlled damage and/or complete damage.

The control of the level of oxidation and the amount of damage can be monitored using a control sample having a predictable, known response to certain ideal operational parameters.

The methods described above can be utilized to determine structural information about a target molecule or a biological molecule. Biological molecules can include secondary, tertiary, and quaternary structure that precludes solvent interaction with various parts of the biological molecule.

Free Radical Generation Devices

This disclosure provides free radical generation devices. The free radical generation devices can include a free radical source and a free radical transmitting barrier positioned in a direction relative to the free radical source. The free radical source can generate one or more free radicals, as described elsewhere herein. The free radical source can be configured to emit at least one free radical of the one or more free radicals in a direction of the free radical transmitting barrier and with a sufficient velocity to travel through the free radical transmitting barrier.

The free radical generation device can provide a predictable amount of free radicals when operably connected to a system, such as those described herein, and controlled with known parameters.

A host of configurations are contemplated, such as a plasma electrode and a ground electrode positioned at opposite ends of a tube comprising a barrier material as described elsewhere herein; a variety of plasma sources coupled with a barrier material positioned to selectively filter the produced free radicals—the plasma sources including but not limited to electron cyclotron resonance (ECR), inductively coupled plasma (ICP), capacitively coupled plasma (CCP), neutral loop discharge (NLD), dielectric barrier discharge, corona discharge, parallel plate reactor, slot plane antenna reactor, etc., or any other plasma source described elsewhere herein; and the like. Electrode spacing can be varied by someone skilled in the art to optimize the radical production which is often necessary when the composition of the free radical precursor material is changed.

Kits

This disclosure provides kits.

In one aspect, a kit can comprise a plurality of free radical generation devices and an identifier. The plurality of free radical generation devices each as described elsewhere herein, wherein a) the free radical sources of at least two of the plurality of free radical generation devices are configured to generate different amounts of free radicals, b) the free radical transmitting barriers of at least two of the plurality of free radical generation devices have known different free radical transmission properties, or c) a combination thereof. The identifier can be configured to correlate a specific free radical generation device of the plurality of free radical generation devices with the different amounts of free radicals or the different free radical transmission properties for the specific free radical generation device. In certain aspects, the identifier can be configured to identify and amount of free radicals that can be generated by a specific free radical generation device given a known configuration of a system in which the specific free radical generation device is used (for example, a known voltage or other free radical generation property described elsewhere herein).

In another aspect, a kit can comprise a plurality of free radical transmitting barriers and an identifier. The plurality of free radical transmitting barriers can have different known responses to interaction with a free radical species. The identifier can be configured to correlate a specific free radical transmitting barrier of the plurality of free radical transmitting barriers with the known response for the specific free radical transmitting barrier. The different known responses can be different known free radical transmission properties. This kit can be used in a fashion similar to a set of optical filters, where one of the plurality of free radical transmitting barriers can be swapped for another in order to increase or decrease relative attenuation of free radicals. By using this kit, increased control of free radical exposure can be achieved without extensive change to the operational parameters associated with the generation of the free radicals.

EXAMPLE 1

Figure 6:
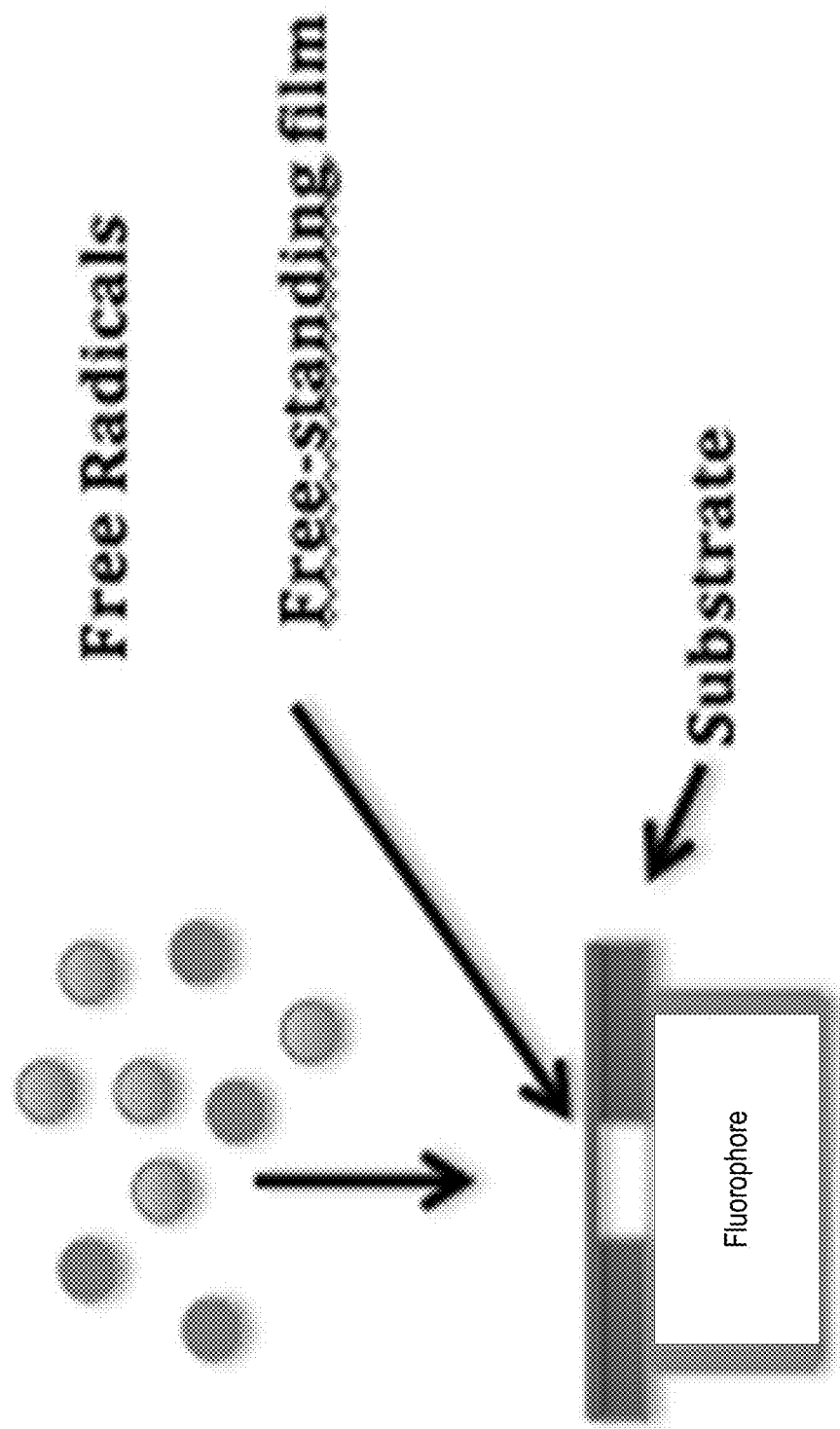
FIG. 6 is a schematic of an experimental setup used in Example 1.

An experimental setup shown in FIG. 6 was used to study the transmission properties of free radicals produced by a plasma through silicon nitride (SiN). SiN dielectric freestanding films of thicknesses 50 nm and 100 nm were used in this Example. Other thickness values may be suitable in certain circumstances.

As shown in FIG. 6, the freestanding films were used to cover the wells of a microtitre plate containing Alexa Fluor™ fluorophore, available commercially from ThermoFisher Scientific, Waltham, Mass. A plasma was produced using air as a feedgas, because Alexa Fluor™ selectively reacts with reactive oxygen species (ROS). When radicals interact with this fluorophore, the fluorophore is modified leading to a decrease in fluorescence (i.e., the fluorophore is quenched). Using a conventional fluorimeter, the fluorescence of the fluorophore was measured before and after plasma exposure. The fluorophore was exposed to the plasma without a freestanding film intervening and with the 50 nm and 100 nm films intervening. The fluorophore was exposed to the plasma under these conditions in separate iterations for 15 minutes, 30 minutes, and 60 minutes. Other exposure times can be suitable in certain circumstances.

Figure 7:
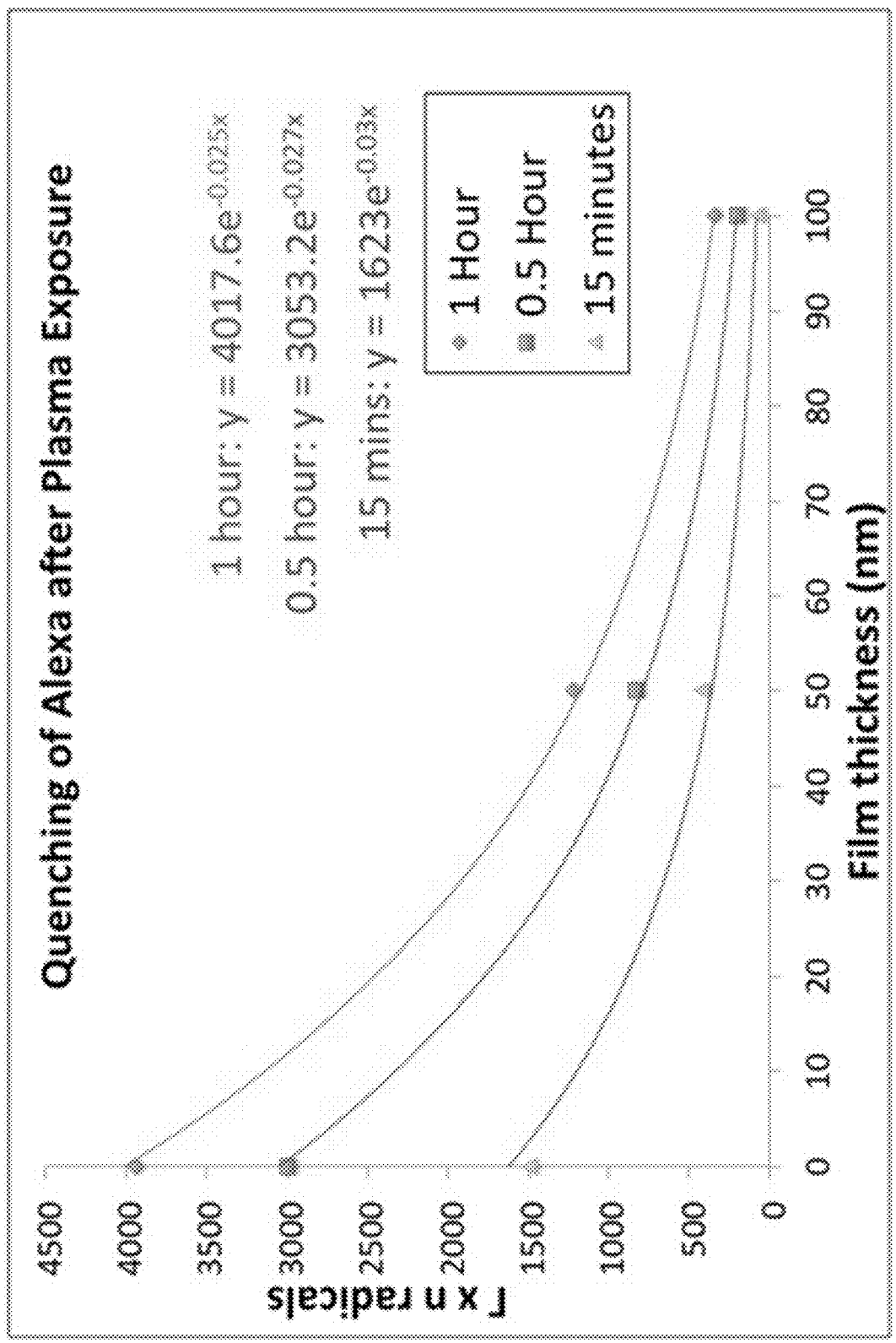
FIG. 7 is a plot of data acquired in Example 1.

Referring to FIG. 7, the results are shown. Using the fluorometric data, the residual number of radicals that penetrated through the SiN membrane were plotted as a function of the thickness of the freestanding film. Note that the exposure time of 60 minutes caused an unusual response in the fluorophore, which limited the overall quenching, but did not impact the efficacy of the technique. An exponential fit was used to fit the data, which allowed information to be extracted about the absorption length of the oxygen radicals through the SiN film. The results indicate that the absorption length of oxygen radicals increased slightly with plasma exposure times. Without wishing to be bound by any particular theory, it is believed that oxidization of the top layers of the SiN membrane lowers the density of the film and allows easier radical passage.

Although the invention has been described in considerable detail with reference to certain aspects, one skilled in the art will appreciate that the present invention can be practiced by other than the described embodiments, which have been presented for purposes of illustration and not of limitation. Therefore, the scope of the appended claims should not be limited to the description of the embodiments contained herein.

We claim:
1. A system comprising:
a free radical source configured to generate a plurality of free radicals;
an interaction chamber comprising a free radical detection species;
a material mount configured to receive a material of interest, the material mount positioning the material of interest between the free radical source and the interaction chamber; and
a material property analyzer, an electrical property analyzer, a chemical property analyzer, a mechanical property analyzer, or a structural property analyzer operatively coupled to the interaction chamber to analyze the free radical detection species,
wherein the free radical detection species undergoes a measurable change in at least one property after interaction with one or more of the plurality of free radicals,
wherein at least a portion of the plurality of free radicals move from the free radical source, through the material of interest when mounted in the material mount, and into the interaction chamber,
wherein the material property analyzer, the electrical property analyzer, the chemical property analyzer, the mechanical property analyzer, or the structural property analyzer measures the measurable change and characterizes one or more properties of the material of interest using the measurable change.

2. The system of claim 1, wherein the free radical source generates the plurality of free radicals via a plasma.

3. The system of claim 1, the system further comprising a power supply and a control system operatively coupled to the free radical source, the free radical source comprising a plasma electrode and a ground electrode.

4. The system of claim 3, wherein the control system is in electronic communication with the power supply, the ground electrode, and the plasma electrode, the control system configured to utilize electrical power from the power supply with the plasma electrode and the ground electrode to generate the plasma.

5. The system of claim 1, the system further comprising a free radical generation chamber, wherein the free radical source is positioned in the free radical generation chamber.

6. The system of claim 5, wherein the free radical generation chamber is configured to retain a liquid, a gas, or a vacuum.

7. The system of claim 1, wherein the interaction chamber is configured to retain a liquid or a gas.

8. The system of claim 1, wherein the interaction chamber comprises a chemically and biologically inert inner surface.

9. The system of claim 1, wherein the material of interest is a thin film.

10. The system of claim 9, wherein the thin film is freestanding.

11. The system of claim 9, wherein the thin film is mounted on a substrate.

12. The system of claim 11, wherein the substrate has a thickness of between 1 nm and 10 cm.

13. The system of claim 11, wherein the substrate comprises a substrate material selected from the group consisting of silicon nitride, silicon dioxide, silicon oxynitride, hafnium oxide, silicon carbide, silicon carbon nitride, silicon carbon hydroxide, and combinations thereof.

14. The system of claim 9, wherein the thin film has a thickness of between 1 nm and 5 cm.

15. The system of claim 1, the system further comprising a plurality of additional interaction chambers, each of the plurality of additional interaction chambers comprising an additional free radical detection species, wherein the material property analyzer, the electrical property analyzer, the chemical property analyzer, the mechanical property analyzer, or the structural properly analyzer is operatively coupled to each of the plurality of additional interaction chambers to analyze each of the additional free radical detection species.

16. The system of claim 15, the system further comprising one or more additional free radical sources that each are configured to generate one or more additional free radicals.

17. The system of claim 16, wherein each of the one or more additional free radical sources is positioned in an additional free radical generation chamber.

18. The system of claim 15, the system further comprising one or more additional material mounts, each of the one or more additional material mounts positioned between the free radical source or one of the one or more additional free radical sources and one of the plurality of additional interaction chambers, each of the one or more additional material mounts configured to receive an additional material of interest.

* * * * *